United States Patent
Liu et al.

(10) Patent No.: US 11,705,224 B2
(45) Date of Patent: Jul. 18, 2023

(54) METHOD FOR SCREENING OF TARGET-BASED DRUGS THROUGH NUMERICAL INVERSION OF QUANTITATIVE STRUCTURE-(DRUG)PERFORMANCE RELATIONSHIPS AND MOLECULAR DYNAMICS SIMULATION

(71) Applicant: PUKYONG NATIONAL UNIVERSITY INDUSTRY—UNIVERSITY COOPERATION FOUNDATION, Busan (KR)

(72) Inventors: Jay Liu, Busan (KR); Myung Gi Yi, Busan (KR); Petar Zuvela, Woodlands (SG)

(73) Assignee: Pukyong National University Industry-University Cooperation Foundation, Busan (KR)

( * ) Notice: Subject to any disclaimer, the term of this patent is extended or adjusted under 35 U.S.C. 154(b) by 688 days.

(21) Appl. No.: 16/628,976

(22) PCT Filed: Jul. 6, 2017

(86) PCT No.: PCT/KR2017/007269
§ 371 (c)(1),
(2) Date: Jun. 8, 2020

(87) PCT Pub. No.: WO2019/009451
PCT Pub. Date: Jan. 10, 2019

(65) Prior Publication Data
US 2020/0342960 A1    Oct. 29, 2020

(30) Foreign Application Priority Data
Jul. 6, 2017  (KR) .................... 10-2017-0085981

(51) Int. Cl.
G16C 20/50 (2019.01)
G16B 15/30 (2019.01)
(Continued)

(52) U.S. Cl.
CPC .............. *G16C 20/50* (2019.02); *G16B 15/30* (2019.02); *G16C 10/00* (2019.02); *G16C 20/20* (2019.02)

(58) Field of Classification Search
CPC ........ G16C 20/50; G16C 10/00; G16C 20/20; G16B 15/30
See application file for complete search history.

(56) References Cited

U.S. PATENT DOCUMENTS

2004/0107054 A1   6/2004  Labute
2004/0199334 A1   10/2004 Kovedsi et al.
(Continued)

FOREIGN PATENT DOCUMENTS

| JP | 4377691 B2 | 12/2009 |
|----|------------|---------|
| KR | 10-1128425 B1 | 3/2012 |
| KR | 10-2015-0100152 A | 9/2015 |

OTHER PUBLICATIONS

International Search Report of corresponding PCT Application No. PCT/KR2017/007269—4 pages (dated Apr. 2, 2018).
(Continued)

*Primary Examiner* — Michael Jung
(74) *Attorney, Agent, or Firm* — Knobbe Martens Olson & Bear LLP

(57) ABSTRACT

Disclosed is a target-based drug screening method using inverse quantitative structure-(drug)performance relationships (QSPR) analysis and molecular dynamics simulation. The method includes modeling a molecular structure of a test compound group against a target molecule, obtaining a quantitative structure-(drug)performance relationships
(Continued)

(QSPR) of the test compound group, acquiring the optimal pharmacophore of a novel target-based drug through a numerical inversion of the QSPR, and selecting drug candidates having a molecular structure similar to the optimum pharmacophore from the test compound group.

6 Claims, 10 Drawing Sheets

(51) Int. Cl.
*G16C 10/00* (2019.01)
*G16C 20/20* (2019.01)

(56) References Cited

U.S. PATENT DOCUMENTS

| | | | |
|---|---|---|---|
| 2005/0177318 A1* | 8/2005 | Young | G16C 20/50 702/27 |
| 2005/0240355 A1 | 10/2005 | Brown et al. | |
| 2013/0184462 A1 | 7/2013 | Srivastava et al. | |
| 2014/0297201 A1* | 10/2014 | Knorr | G01N 30/8693 702/28 |
| 2016/0378912 A1* | 12/2016 | Ragno | G16C 20/60 506/8 |
| 2017/0206308 A1* | 7/2017 | Fleishman | G16B 35/10 |
| 2018/0253453 A1* | 9/2018 | Botea | G16C 20/40 |

OTHER PUBLICATIONS

Leelananda et al., "Computational methods in drug discovery", Beilstein Journal of Organic Chemistry, vol. 12—25 pages (2016).
Miyao et al., "Inverse QSPR/QSAR Analysis for Chemical Structure Generation (from y to x)", Journal of Chemical Information and Modeling, vol. 56—14 pages (2016).
Žuvela et al., "Prediction and Design of Novel Antitumor Pharmaceuticals Using Chemometrics and Computational Chemistry", In: 18th International Symposium on Advances in Extraction Technologies (ExTech'2016) and the 22nd International Symposium on Separation Science (ISSS'2016), Torun, Poland, Jul. 3-6, 2016, pp. 5/26-24/26.

* cited by examiner

METHOD FOR SCREENING OF TARGET-BASED DRUGS THROUGH NUMERICAL INVERSION OF QUANTITATIVE STRUCTURE-(DRUG)PERFORMANCE RELATIONSHIPS AND MOLECULAR DYNAMICS SIMULATION

CROSS REFERENCE TO RELATED APPLICATIONS

This is a U.S. National Stage Application, filed under 35 U.S.C. 371, of International Patent Application No. PCT/KR2017/007269, filed on Jul. 6, 2017, which claims priority to Korean Patent Application No. 10-2017-0085981 filed on Jul. 6, 2017, contents of both of which are incorporated herein by reference in their entireties.

TECHNICAL FIELD

The present invention relates to a drug screening method for determining a novel target-based drug. More specifically, the present invention relates to a drug screening method for determining a novel target-based drug by finding an optimal pharmacophore of a drug through numerical inversions of a quantitative structure-(drug)performance relationships (QSPR) model of a test compound group, and through molecular dynamics simulation on complexes each being composed of a target molecule and a candidate compound.

BACKGROUND ART

For many years, drug discovery has been dominated by structure-based methods that focus on development and analysis of compounds themselves. In recent years, with advances in technology, in silico prediction technology such as target-based drug design and ligand-based virtual screening has been widely used during the initial stage of research and development of a novel drug. The in silico prediction technology is a method of virtually predicting active compounds against a specific biological target with high accuracy by using a computer.

The food and drug administration (FDA) in USA encourages pharmaceutical companies to use in silico computer modeling technology for evaluation of drug efficacy and side-effects. The use of an appropriate in silico prediction model can significantly reduce clinical tests required in a traditional drug approval process. In fact, the FDA assumes that a 10% improvement in accuracy of identification of targets for a test compound as novel drug can reduce the cost of drug discovery by an amount of 100 of millions to 1 billion dollars.

Therefore, global leading pharmaceutical companies are developing computer-based prediction systems using experimental data of metabolic screening and absorption screening before entering a preclinical study stage. For example, Novartis, a multinational pharmaceutical company, is known to have developed a computer program called ToxCheck in 2003 to solve toxicity-related problems. However, it is difficult to determine the technological level of the company because the program has not been commercially available. In addition, in recent years, the establishment of a large number of institutions/entities that evaluate interactions and toxicity of drugs proves the need of the development of prediction models.

In addition, in order to create a prediction model using a computer, investments for collection and accumulation of necessary experimental data are being made mainly in the United States, Germany, the United Kingdom, and Japan.

DISCLOSURE

Technical Problem

The present invention has been made due to the above-described need, and an objective of the present invention is to provide a target-based drug screening method capable of significantly reducing the cost of drug discovery and avoiding synthesis of false compounds and wasteful pharmaceutical tests of the false compounds by using numerical inversions of a quantitative structure-(drug)performance relationships model of a test compound group against a target molecule, and by performing molecular dynamics simulation on complexes each being composed of a drug candidate and a target molecule during discovery of a novel drug.

Technical Solution

In order to accomplish the above objective, according to one aspect of the present invention, there is provided a drug screening method for determining a novel target-based drug by using a numerical inversion of a quantitative structure-(drug)performance relationships (QSPR) model and molecular dynamics simulation, the method including: modeling a molecular structure of a test compound group against a target molecule; obtaining a quantitative structure-(drug)performance relationships (QSPR) model between the molecular structure and the performance of the test compound group; acquiring an optimal pharmacophore of a novel target-based drug through a numerical inversion of the QSPR model; and screening a group of drug candidates having a molecular structure similar to the optimal pharmacophore to determine the novel target-based drug.

In addition, the modeling of the molecular structure of the test compound group may include a compound selection process of selecting the test compound group, a data collection process of collecting chemical and biological experimental data of the test compound group, and a molecular structure modeling process of optimizing the molecular structure by modeling the molecular structure of the test compound group on the basis of the experimental data.

In addition, obtaining the quantitative structure-(drug) performance relationships (QSPR) model may include a calculation process of calculating molecular descriptors from the molecular structure and a QSPR modeling process of modeling the quantitative structure-(drug)performance relationships (QSPR) model by using the molecular descriptors.

In addition, in the quantitative structure-activity relationships (QSPR) model, the performance may include one or more drug performances selected from among biological activity, inhibitory activity, lipophilicity, toxicity, metabolic stability and blood-brain barrier permeability.

In addition, the QSPR modeling process may select a part of the molecular descriptors by using a genetic algorithm and then model the quantitative structure-(drug)performance relationships by using the selected molecular descriptors.

In addition, in the acquiring of the optimal pharmacophore of the novel drug, the optimal pharmacophore of the novel drug may be obtained through the numerical inversion performed according to Expression 1 or Expression 2.

$$x^* = \arg\max \log \hat{k}_w$$

$$\text{s.t } \log \hat{k}_w = C\hat{t}$$

$$\hat{t} = Px$$

$$\hat{t}^T S_t^{-1} t \leq c_1$$

$$\|P\hat{t} - x\| \leq c_2 \quad \text{Expression 1}$$

x: a vector of molecular descriptors of a novel drug x*: a vector of optimal molecular descriptors of a novel drug candidate calculated through mathematical programming based on the above mathematical expression C: output variable loading matrix of partial least squares (PLS)

t: a PLS score vector of input variables (where the input variables are molecular descriptors x)

P: PLS loading matrix

^: value predicted by PLS model $S_t$: sample covariance matrix of t $c_1$, $c_2$: appropriate constant $$x^* = \arg\max \sqrt{(\log \hat{k}_w - \log k_{w,ref})^2 + (\log \hat{k}_i - \log k_{i,ref})^2} \quad \text{[Expression 2]}$$

$$\text{s.t } [\log \hat{k}_w, \log \hat{k}_w]^T = C\hat{t}$$

$$\hat{t} = Px$$

$$\hat{t}^T S_{t^{-1}} t \leq c_1$$

$$|P\hat{t} - x| \leq c_2$$

x: a vector of molecular descriptors of a novel drug x*: a vector of optimal molecular descriptors of a novel drug candidate calculated through mathematical programming based on the above mathematical expression C: output variable loading matrix of partial least squares (PLS)

a PLS score vector of input variables (where the input variables are molecular descriptors x)

P: PLS loading matrix

^: value predicted by PLS model $S_t$: sample covariance matrix of t $c_1$, $c_2$: appropriate constant $\log k_{w,ref}$: lipophilicity value set by user $\log k_{i,ref}$: activity value set by user In addition, the screening of the group of drug candidates may include a process of rating each of the drug candidates according to the Euclidean distance between the optimum pharmacophore of the novel drug and the molecular structure of each of the drug candidates and a process of selecting drug candidates which are rated equal to or higher than a predetermined level from among the drug candidates in the candidate group.

In addition, the method may further include a step of verifying the novel target-based drug, which is performed after the screening of the group of drug candidates. The verifying may be performed through molecular dynamics simulation of complexes each being composed of one of the selected drug candidates and the target molecule.

Advantageous Effects

The drug screening method according to the present invention can be applied to all kinds of drugs and target molecules, can be applied to the performances of all kinds of drugs, and can significantly reduce computations for in silico experiments and save time and manpower for drug discovery.

BEST MODE

Hereinafter, the present invention will be described in detail. Since the following description is provided for detailed description of one embodiment of the present invention, the scope of the present invention as defined by the appended claims is not limited to the embodiment although definite or limiting terms and expressions are used in the description. In describing one embodiment of the present invention, well-known functions or constructions will not be described in detail when they may obscure the gist of the present invention.

Figure 1:
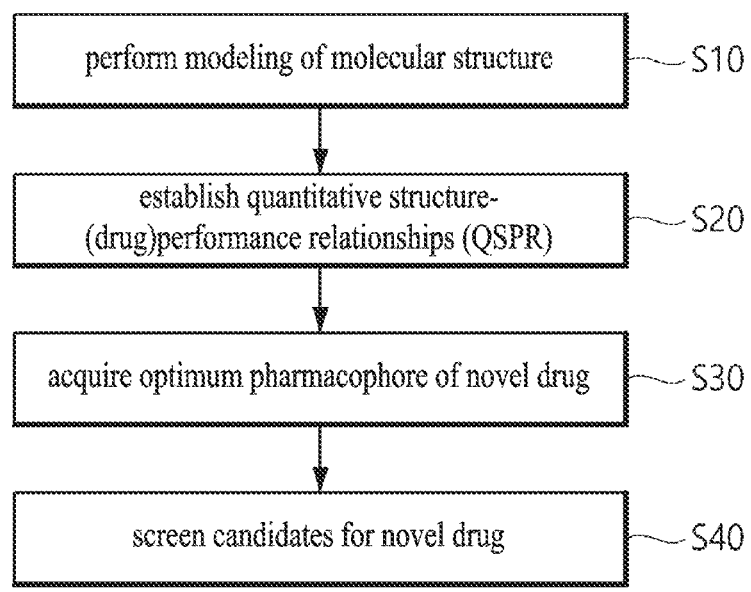
FIG. 1 is a block diagram of a drug screening method according to one embodiment of the present invention.

FIG. 1 is a block diagram of a drug screening method according to one embodiment of the present invention.

Referring to FIG. 1, the drug screening method according to one embodiment of the present invention includes a molecular structure modeling step S10, a quantitative structure-(drug)performance relationships (QSPR) model creation step S20, an optimal pharmacophore acquisition step S30, and a drug candidate group screening step S40. The present invention may be embodied in an implementation form that can be executed on a computer.

Figure 2:
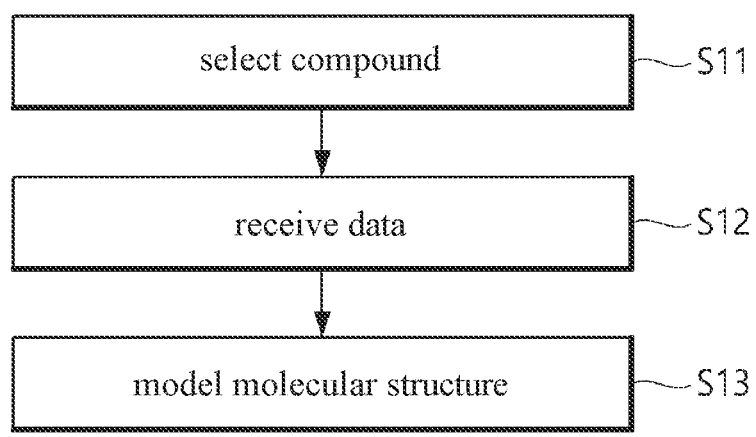
FIG. 2 is a block diagram illustrating a step of modeling a molecular structure according to the present invention.

FIG. 2 is a block diagram illustrating a step of modeling a molecular structure according to the present invention.

The molecular structure modeling step S10 is to model the molecular structures of compounds in a test compound group to be tested against a target molecule. Examples of the target molecule include a protein, an enzyme, DNA, and RNA. The test compound refers to a compound that inhibits the activity of the target molecule or alters the target molecule.

Specifically, referring to FIG. 2, the molecular structure modeling step S10 includes a compound selection process S11, a data reception process S12, and a molecular structure modeling process S13.

The compound selection process S11 is to select a group of test compounds. In this process, test compounds that can inhibit the activity of the target molecule or alter the target molecule are selected.

The data reception process S12 is to receive biological and chemical experimental data of the test compounds. The data includes the boiling point, freezing point, polarity, solubility, reactivity, toxicity, selectivity, and the like of each test compound.

In addition, the molecular structure modeling process S13 is to model the molecular structure of the test compound group on the basis of the experimental data and optimize the molecular structure by using quantum chemistry.

Figure 3:
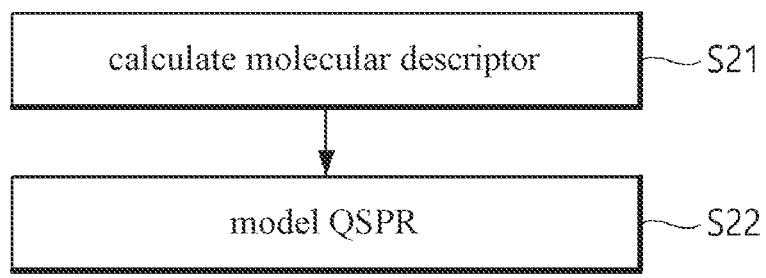
FIG. 3 is a block diagram illustrating a step of establishing a quantitative structure-(drug)performance relationships model according to the present invention.

FIG. 3 is a block diagram illustrating a step of establishing a quantitative structure-(drug)performance relationships model according to the present invention.

The quantitative structure-(drug)performance relationships model creation step S20 is to obtain relationships between the structures and the performances of the test compound group.

Specifically, referring to FIG. 3, the quantitative structure-(drug)performance relationships model creation step S20 includes a molecular descriptor calculation process S21 and a quantitative structure-(drug)performance relationships modeling process S22.

The molecular descriptor calculation process S21 is to calculate 4000 or more molecular descriptors on the basis of the molecular structure.

In addition, the quantitative structure-(drug)performance relationships (QSPR) modeling process S22 is to obtain a QSAR model on the basis of the molecular descriptors.

Specifically, in the QSPR modeling process S22, a genetic algorithm (GA) is applied to the molecular descriptors resulting from the calculation process S21 to select a part of the molecular descriptors, and then the quantitative structure-(drug)performance relationships is modeled by using the selected molecular descriptors.

Here, the genetic algorithm (GA) is the most popular optimization algorithm that is based on the direct inference of natural selection and the Darwinian evolution of genes in biological systems, and it can be successfully applied to various processes such as data mining and optimization.

In the present invention, QSPRs are modeled by using molecular descriptors calculated theoretically, rather than using 2-dimensional molecular descriptors that are often used in conventional quantitative structure-activity relationships (QSAR). Therefore, a more accurate description of the molecular structure of a target-based drug is possible.

In addition, in the quantitative structure-(drug)performance relationships (QSPR), the performance may include one or more performances selected from among biological activity, inhibitory activity, lipophilicity, toxicity, metabolic stability and blood-brain barrier permeability. The relationships between each of the various performances and the molecular structure are obtained and used in the subsequent step.

In the present invention, since nearly 4000 molecular descriptors are used to model the structure-performance relationships, the selection of the molecular descriptors, which has the greatest impact on the activity prediction of drug, and regression modeling can be simultaneously performed.

In addition, the optimal pharmacophore acquisition step S30 is to obtain the optimal pharmacophore of a novel drug through numerical inversions of the QSPRs.

Specifically, the optimal pharmacophore acquisition step S30 is to obtain the optimal pharmacophore which maximizes the performance (e.g., lipophilicity) of a drug through the numerical inversion which is performed according to Expression 1.

$$x^* = \arg\max \log \hat{k}_w$$
$$\text{s.t } \log \hat{k}_w = C\hat{t}$$
$$\hat{t} = Px$$
$$\hat{t}^T S_t^{-1} \hat{t} \le c_1$$
$$\|P\hat{t} - x\| \le c_2 \qquad \text{Expression 1}$$

x: a vector of molecular descriptors of a novel drug x*: a vector of optimal molecular descriptors of a novel drug candidate calculated through mathematical programming based on Expression 1

C: output variable loading matrix of partial least squares (PLS)

a PLS score vector of input variables (where the input variables are molecular descriptors x)

P: PLS loading matrix

^: value predicted by PLS model $S_t$: sample covariance matrix of t $c_1, c_2$: appropriate constant In addition, in the optimal pharmacophore acquisition step S30, the optimal pharmacophore having the performance (for example, lipophilicity or activity ($\log k_i$) designated by the user) can be obtained through the numerical inversion performed according to Expression 2.

$$x^* = \arg\max \sqrt{(\log \hat{k}_w - \log k_{w,ref})^2 + (\log \hat{k}_i - \log k_{i,ref})^2} \qquad [\text{Expression 2}]$$
$$\text{s.t } [\log \hat{k}_w, \log \hat{k}_w]^T = C\hat{t}$$
$$\hat{t} = Px$$
$$\hat{t}^T S_{t-1} \hat{t} \le c_1$$
$$|P\hat{t} - x| \le c_2$$

x: a vector of molecular descriptors of a novel drug x*: a vector of optimal molecular descriptors of a novel drug calculated through mathematical programming based on Expression 2

C: output variable loading matrix of partial least squares (PLS)

a PLS score vector of input variables (where the input variables are molecular descriptors x)

P: PLS loading matrix

^: value predicted by PLS model $S_t$: sample covariance matrix of t $c_1, c_2$: appropriate constant $\log k_{w,ref}$: lipophilicity value set by user $\log k_{i,ref}$: activity value set by user In addition, in the optimal pharmacophore acquisition step S30, the optimal pharmacophore having the performance designated by the user can be obtained through the numerical inversion using various objective functions such as Expression 1 or Expression 2.

Figure 4:
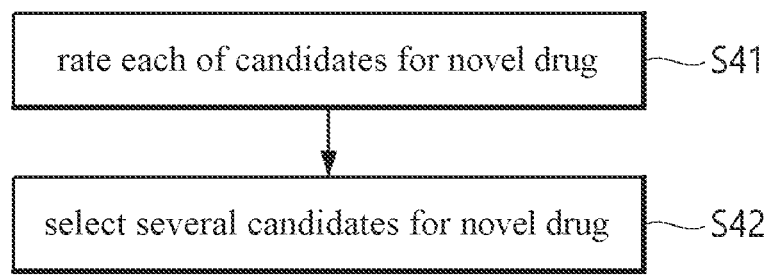
FIG. 4 is a block diagram illustrating a step of screening drug candidates for novel target-based drug, according to the present invention.

FIG. 4 is a block diagram illustrating a step of screening drug candidates for a novel target-based drug, according to the present invention.

The drug candidate group screening step S40 is to select drug candidates having a molecular structure similar to the optimal pharmacophore of the novel drug.

Specifically, referring to FIG. 4, the drug candidate group screening step S40 includes a novel drug candidate group rating process S40 and a novel drug candidate group selection process S41.

In addition, the novel drug candidate group rating process S40 is a process of rating each of the drug candidates in the novel drug candidate group according to the Euclidean distance between the optimal pharmacophore of the novel drug and the molecular structure of each of the drug candidates. A candidate with a shorter Euclidean distance is rated a higher level.

In addition, the novel drug candidate group selection process 41 is a process of selecting drug candidates that are rated equal to or higher than a predetermined level from among all of the candidates in the novel drug candidate group.

Figure 5:
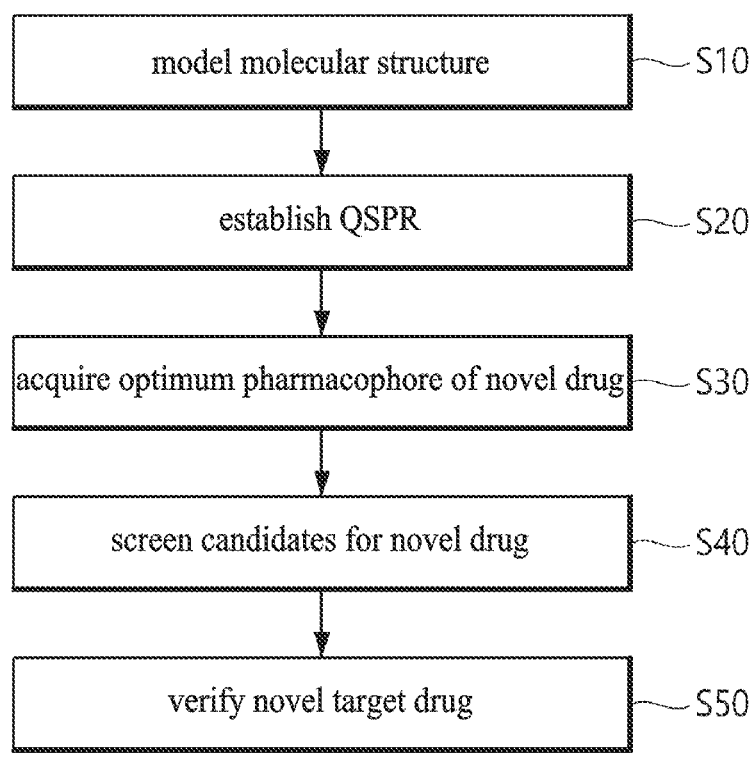
FIG. 5 is a block diagram of a drug screening method according to another embodiment of the present invention.

FIG. 5 is a block diagram of a drug screening method according to another embodiment of the present invention.

On the other hand, referring to FIG. 5, the method of screening drug candidates for a novel target-based drug, which uses numerical inversions of QSPRs and molecular dynamics simulation according to the present invention, may further include a novel target-based drug verification step S50 following the novel drug candidate group screening step S40.

In addition, the novel target-based drug verification step S50 is a step of verifying complexes each being composed of one of the drug candidates for the novel target-based drug, which are selected through the screening step, and the target molecule through molecular dynamics simulation.

Specifically, in the novel target-based drug verification step S50, the optimum candidate for a novel drug against the target molecule can be selected by verifying the drug candidates by performing molecular dynamics simulation on the complexes each being composed of one of the selected drug candidates and the target molecule.

On the other hand, as described above, the present invention checks various structural changes (conformational ensembles) rather than checking only the fixed molecular structures of the drug candidate group and the target molecule by using the molecular dynamics simulation.

The greater details of the present invention will be described below with reference to examples and experiments described below. However, the examples and experiments are intended to describe the present invention in greater detail, and the scope of the present invention is not limited thereto.

Example: Designing and Screening of Sulfonamide Derivatives Inhibiting CA IX (i.e., Target Molecule)

The present invention was applied to designing of sulfonamide derivatives inhibiting CA IX (i.e., target molecule). In the present example, lipophilicity was set as the performance of a drug, and quantitative structure-performance relationships (QSPR) were modeled using partial least squares (PLS).

Liquid chromatography-mass spectrometry (LC-MS) was used to determine the lipophilicity (log $k_w$) values of 14 sulfonamide isomers which were pre-synthesized (Table 1).

TABLE 1

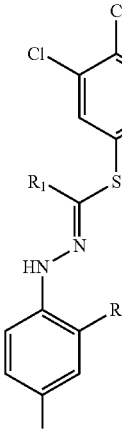

| Compound | $R_1$ | $R_2$ | $\log k_w$ |
|---|---|---|---|
| 1EZ | Et | H | 3.76 |
| 2EZ | Pr | H | 3.52 |
| 3EZ | i-Pr | H | 3.8 |
| 4EZ | i-Pr | $NO_2$ | 3.61 |
| 5EZ | i-Bu | H | 3.68 |
| 6EZ | τ-Bu | H | 3.64 |
| 7EZ | n-C5H11 | H | 3.54 |
| 8EZ | Ph—CH2—CH2 | H | 3.62 |
| 9EZ | Ph | H | 3.41 |
| 10EZ | 4-Cl—Ph | H | 3.6 |
| 11EZ | 4-NO2—Ph | H | 3.56 |
| 12EZ | 4-Me—Ph | H | 3.52 |
| 13EZ | 4-MeO—Ph | H | 3.64 |
| 14EZ | 3-Br,4-OH—Ph | H | 3.49 |

14 Sulfonamide Compounds and their Lipophilicity Values

The molecular structure was optimized through PM3 semi-empirical quantum mechanics and nearly 4000 molecular descriptors were calculated for the optimized structure. This data was divided into a training data set and a test data set. Next, a genetic algorithm combined with the partial least squares method was used for descriptor selection. Thus, a quantitative structure-performance relationships (QSPR) was established on the basis of four molecular descriptors (Table 2).

TABLE 2

| Molecular descriptor | Description |
|---|---|
| $R_{7e+}$ | R maximum auto-correlation of a deviation of 7 weighted by Sanderson electronegativities |
| F10[C-Cl] | Frequency of a (C-Cl) atomic pair at a topological distance n of 10 |
| $H^{6i}$ | H auto-correlation of a deviation of 6 weighted by an ionization potential |
| MLOGP | Moriguchi octanol-water partition coefficient indicating hydrophobicity |

Molecular Descriptor Selected for QSPR Modeling

Figure 6:
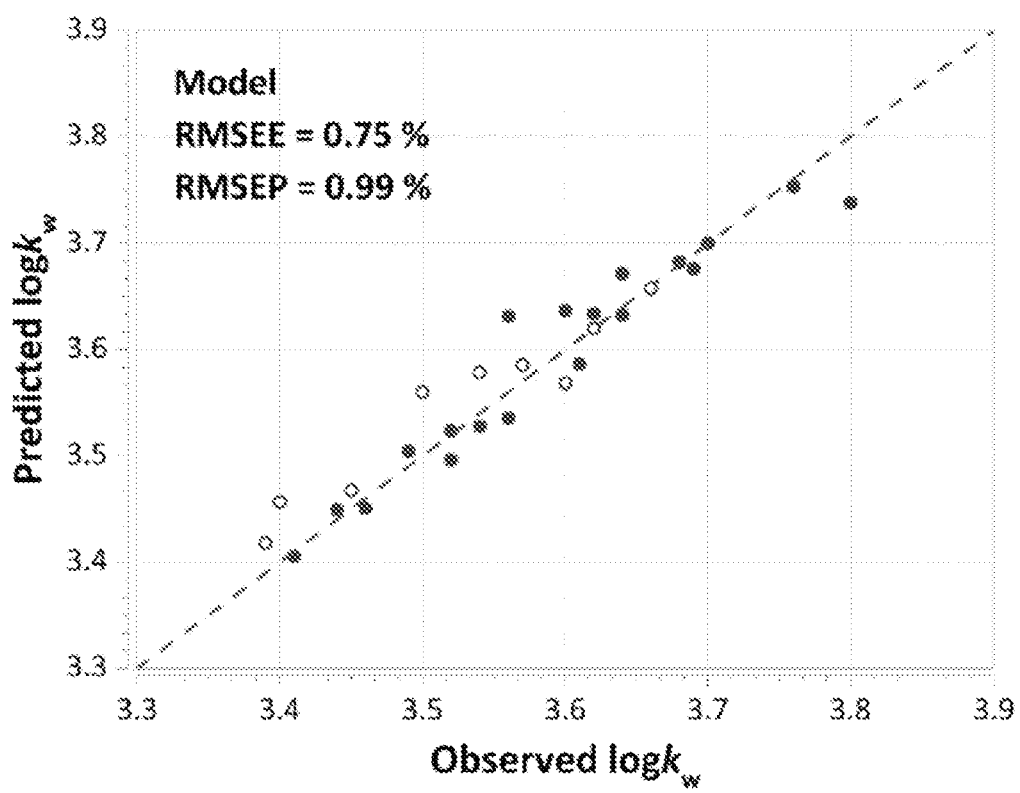
FIG. 6 is a graph illustrating the performance of a quantitative structure-(drug)performance relationships (QSPR) model according to the present invention.
Figure 7:
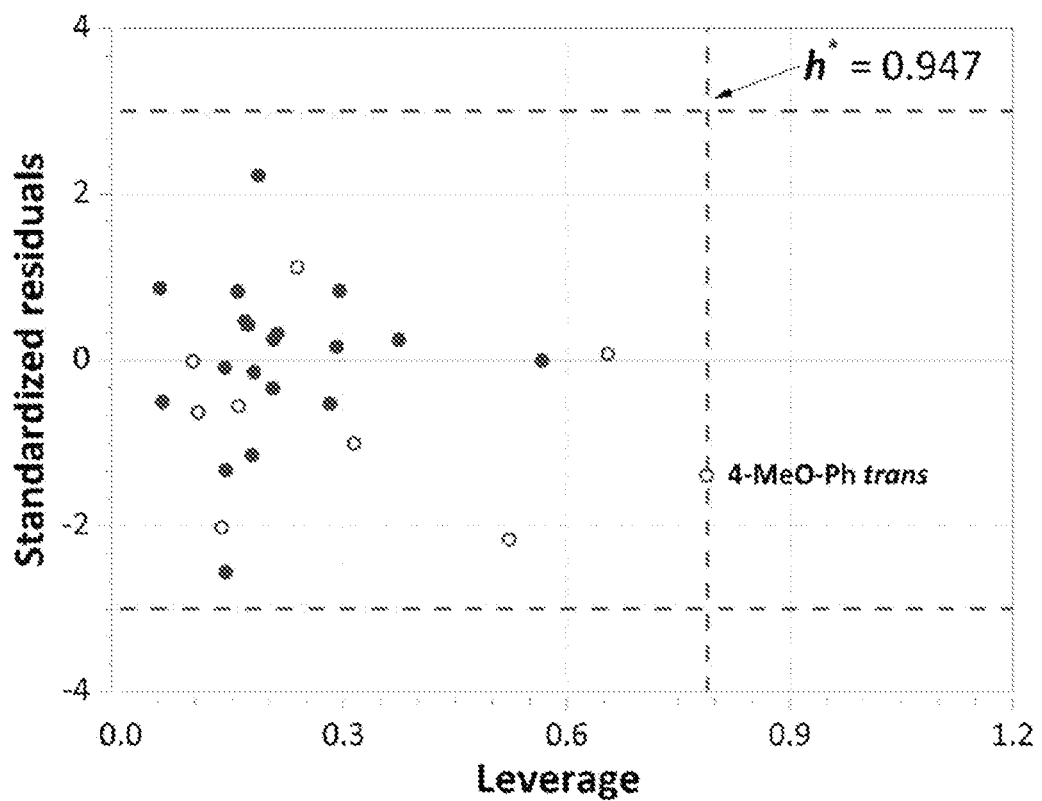
FIG. 7 is a graph illustrating an applicability domain of the QSPR model according to the present invention.

FIG. 6 is a graph illustrating the performance of a quantitative structure-performance relationships (QSPR) model according to the present invention, and FIG. 7 is a graph illustrating an area to which the QSPR model according to the present invention is applicable.

As shown in FIG. 6, the quantitative structure-performance relationships (QSPR) model has a high prediction performance. That is, the root mean squared error of estimation (RMSEE) and the root mean squared error of prediction (RMSEP) respectively exhibit 0.67% and 0.97% for all compounds found within the QSPR applicability domain. As shown in FIG. 7, all data elements of the training data set (marked with ●) and of the test data set (marked with ○) were found to be stable because they were not beyond a control limit.

The developed QSPR model is inverted through numerical optimization having constrains described below.

$$x^* = \arg\max \log \hat{k}_w$$

$$\text{s.t } \log \hat{k}_w = C\hat{t}$$

$$\hat{t} = Px$$

$$\hat{t}^T S_t^{-1} \hat{t} \leq c_1$$

$$\|P\hat{t} - x\| \leq c_2$$

x: a vector of molecular descriptors of a novel drug x*: a vector of molecular descriptor of a novel drug calculated through mathematical programming based on the above expression.

C: output variable (i.e., lipophilicity) loading matrix of partial least squares (PLS)

a PLS score vector of input variables (where the input variables are molecular descriptors x)

P: PLS loading matrix

^: value predicted by PLS model $S_t$: sample covariance matrix of t $c_1$, $c_2$: appropriate constant The optimum molecular descriptors were obtained through this method, and the optimum molecular descriptors were compared against a database of previously generated drug candidates. Each of the drug candidates was then rated according to the Euclidean distance. This procedure yielded 11 drug candidates for a maximum log $k_w$ value of 3.965 (Table 3).

ics simulation of a sulfonamide-CA IX complex was used. In the verification process, it was assumed that the complex was surrounded by water molecules to form a dodecahedron to simulate the movement of the complex in human body fluids.

The molecular dynamics simulation showed that $Zn^{2+}$ ions were coordinated with three histidine residues at the active sites. This was performed to ensure that the function of the CA IX enzyme was not impaired in the simulation.

Figure 9:
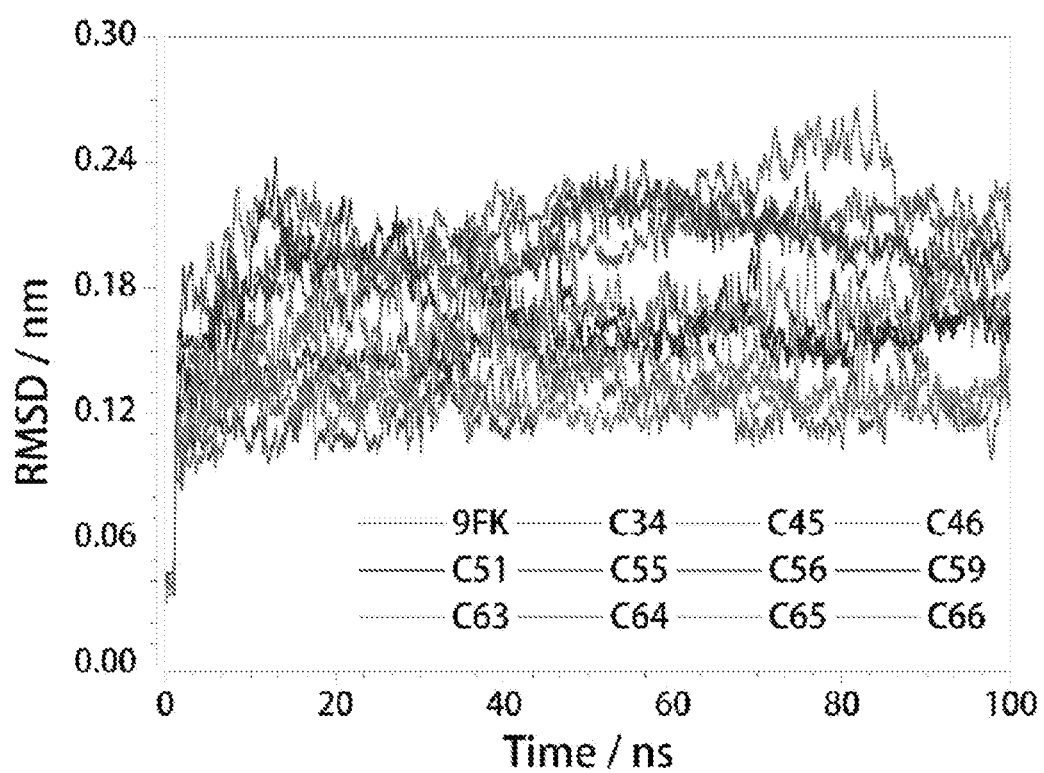
FIG. 9 is a view illustrating the stability of CA IX according to the present invention.

FIG. 9 is a view illustrating the stability of CA IX according to the present invention.

The stability and flexibility of the enzyme were analyzed by calculating the root mean square deviation (RMSD) and the root mean square fluctuation (RMSF). The hydrogen bonds and hydrophobic and hydrophilic interactions were also evaluated.

As shown in FIG. 9, among the 11 complexes, several complexes including C65, C64, or C63 as a ligand exhibited their RMSD value similar to the RMSD value (about 0.1 nm) of a CA IX-FK complex (5-(1-naphthalen-1-yl-1,2,3-triazol-4-yl)thiophene-2-sulfonamide). However, the other complexes exhibited higher RMSD values (about 0.2 nm).

This discrepancy is due to the small size of the 9FK sulfonamide. Since the screened compounds are bulky, the enzyme must match in its form in such a way that it can accommodate the compound within its active site.

Figure 10:
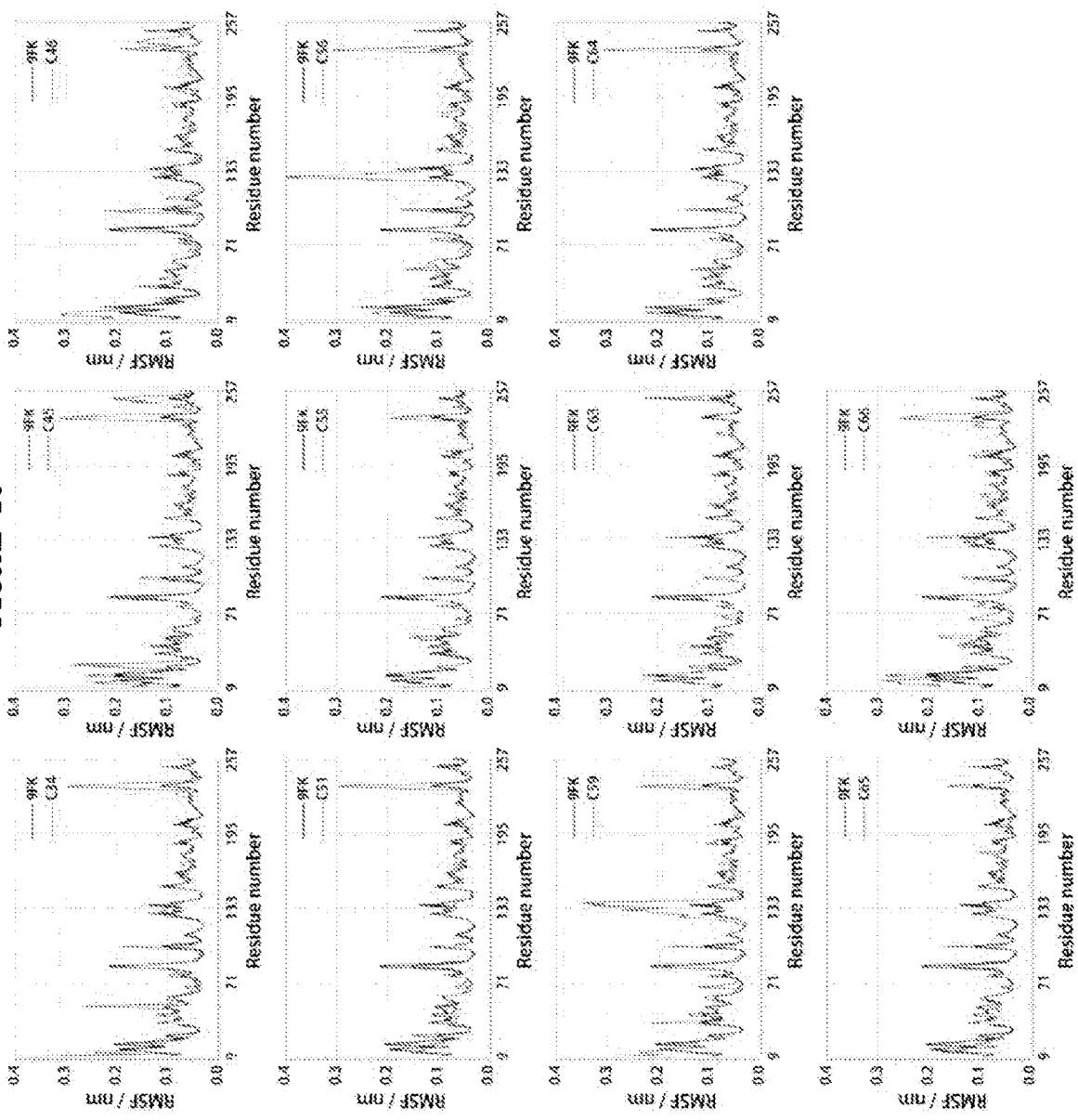
FIG. 10 is a view illustrating the flexibility of CA IX according to the present invention.

FIG. 10 is a view illustrating the flexibility of CA IX according to the present invention.

The root mean square fluctuation (RMSF) was calculated for all the complexes to evaluate the conformational ensemble of CA IX as shown in FIG. 10.

TABLE 3

| | | | | | $R_{7e+}$ | F10[C—Cl] | $H_{6i}$ | MLOGP | |
|---|---|---|---|---|---|---|---|---|---|
| | $\chi^*$ Max, log kw = 3.965 | | | | 0.025 | 5 | 1.040 | 4.529 | |
| Structure | | $R_1$ | $R_2$ | | X value obtained from Database | | | | Distance |
| C45 | $CH_3$ | 4-Cl-butyl | H | 0.020 | 5 | 0.953 | 3.886 | | 0.649 |
| C46 | | 4-Cl-butyl | $NO_2$ | 0.022 | 5 | 1.205 | 3.790 | | 0.757 |
| C65 | Cl | 3-Cl,butoxy | H | 0.015 | 6 | 0.967 | 3.959 | | 1.153 |
| C66 | | 3-Cl,butoxy | $NO_2$ | 0.017 | 6 | 1.241 | 3.885 | | 1.206 |
| C64 | $NH_2$ | 2-Cl,ethoxy | $NO_2$ | 0.029 | 4 | 1.039 | 3.426 | | 1.489 |
| C63 | | 2-Cl,ethoxy | H | 0.021 | 4 | 0.539 | 3.499 | | 1.520 |
| C56 | | 3-Cl,4-OH-phenyl | $NO_2$ | 0.015 | 4 | 0.748 | 3.293 | | 1.616 |
| C55 | | 3-Cl,4-OH-phenyl | H | 0.024 | 4 | 0.500 | 3.366 | | 1.626 |
| C59 | $R_1$ | 3-Cl,4-OH-butyl | H | 0.018 | 4 | 1.474 | 3.147 | | 1.760 |
| C51 | | 4-Me-butyl | H | 0.023 | 3 | 1.206 | 3.886 | | 2.107 |
| C34 | | penthyl | $NO_2$ | 0.017 | 3 | 0.756 | 3.715 | | 2.178 |

Figure 8:
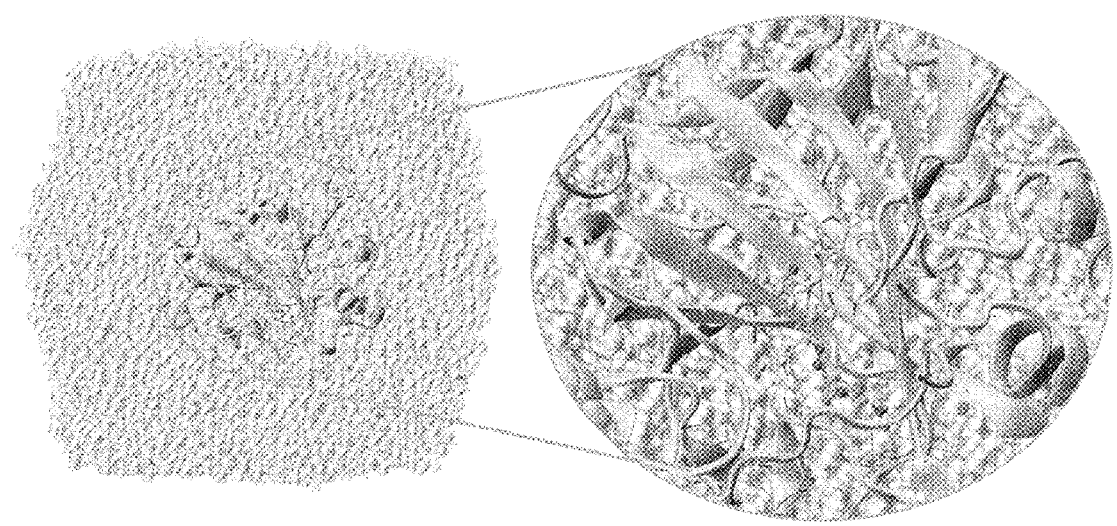
FIG. 8 is a view illustrating images resulting from molecular dynamics simulation of a complex of sulfonamide and carbonic anhydrase (CA) IX, according to the present invention.

Euclidean Distance Between Abnormal Drug Designed by Structure-Performance Relationships Model and Each of Candidate Compounds in Database FIG. 8 is a view illustrating images resulting from molecular dynamics simulation of a complex of sulfonamide and carbonic anhydrase (CA) IX, according to the present invention.

In order to verify the derived candidate compounds for a target-based drug, as shown in FIG. 8, the molecular dynam- The results showed that the enzyme was the most stable in the CA IX-9FK complex. All the other complexes have a similar pattern of RMSF shapes. However, in most cases, higher RMSF values were exhibited in two typical regions: (i) flexible N ends (residues 9 to 20) and (ii) flexible loops (residues 230-240).

The hydrogen bonding network found in the CA IX structure was analyzed to determine the cause of the difference in RMSF value. To this end, the percentage of hydrogen bonds that are formed was calculated through simulation (Table 4). It was found that a hydrogen bond was formed in each of the W9-H68, A133-R136, and R136-G139 bond pairs.

C65 ligand showed very similar characteristics except for their interaction with a compound E106. C66, in contrast, is the most different complex from the CA IX-9FK complex.

TABLE 4

| Bond pair | C45 | C46 | C65 | C66 | C64 | C63 | C56 | C55 | C59 | C51 | C34 | 9FK |
|---|---|---|---|---|---|---|---|---|---|---|---|---|
| W9-H68 | 0.04 | 1.73 | 67.01 | 2.77 | 35 | | 21.77 | 9.09 | 0.41 | 26.07 | 48.06 | 0 | 80.45 |
| A133-R136 | 43.55 | 49.71 | 49.04 | 36.07 | 48.71 | 38.48. | 8.12 | 44.04 | 12.07 | 52.3 | 2.69 | 40.09 |
| R136-G139 | 46.17 | 45.43 | 47.47 | 30.65 | 51.81 | 32.83 | 16.7 | 38.64 | 2.12 | 55.2 | 0.96 | 38.04 |
| S237-P234 | 56.47 | 44.01 | 64.93 | 30.11 | 33.26 | 0 | 67.82 | 63.49 | 67.11 | 67.17 | 46.47 | 92.14 |
| S237-G233 | 69.42 | 0 | 66.81 | 76.46 | 34.86 | 78.51 | 65.51 | 55.86 | 55.51 | 46.92 | 68.82 | 83.82 |
| L249-R252 | 46.75 | 66.86 | 3.66 | 66.4 | 70.65 | 20.36 | 69.95 | 85.47 | 68 | | 89.04 | 80.53 | 82 |

Percentage of Hydrogen Bonds Formed in Simulation

The stability of the designed sulfonamide derivatives at the active site of the CA IX has a significant impact on the interaction. For this reason, changes in the conformation and flexibility of enzymes are considered. Their flexibility was observed by analyzing the root mean square deviation (RMSD) value when overlaying the conformations first in 22.06 ns. The results showed that all of the ligands were quite stable at the active site.

The analysis of the interactions between CA IX and the designed sulfonamide derivatives and between CA IX and 9FK was performed in a manner of calculating the percentage of ligand-amino residue interactions (Table 5) and then calculating the average number of atoms and residues within a ligand coverage of 0.35 nm throughout the simulation (Table 6).

Only two of the seven residues that interact with a ligand were conserved. Stronger hydrophobic and hydrophilic interactions were observed for the simulation of other complexes.

As noted above, according to the example, 14 novel drug candidates were proposed through an inverse quantitative structure-performance relationships analysis, and molecular dynamics simulations were performed on 11 of the 14 candidates. As a result, all of the 11 candidates have been found to be suitable for the inhibition of CA IX than sulfonamide which is a baseline compound.

In addition, all hydrophobic and hydrophilic interactions between substitution groups and active sites were carefully analyzed. Since crystallization of CA IX-ligand complexes is very difficult due to the complex membrane binding structures of enzymes, such an analysis can provide insight into and guidance for future synthesis.

TABLE 5

| Residue | C45 | C46 | C65 | C66 | C64 | C63 | C56 | C55 | C59 | C51 | C34 | 9FK |
|---|---|---|---|---|---|---|---|---|---|---|---|---|
| T200 | 60.47 | 92.22 | 78.73 | n.a. | 98.02 | 82.95 | 98.02 | 100 | 99.19 | n.a. | 99.34 | 100 |
| E106 | n.a. | 100 | n.a. | n.a. | n.a. | 32.24 | 97.01 | 100 | n.a. | n.a. | 100 | 100 |
| Q92 | 99.94 | n.a. | 38.33 | 84.48 | 99.42 | 93.23 | 95.43 | 62.05 | n.a. | 91.77 | 80.81 | 71.97 |
| W210 | n.a. | 31.74 | 30.7 | n.a. | 81.86 | n.a. | n.a. | 65.91 | 100 | 96.02 | 99.8 | 64.09 |
| L134 | 66.68 | n.a. | 53.46 | n.a. | n.a. | n.a. | n.a. | n.a. | 71.83 | 58.6 | n.a. | 59.09 |
| P203 | 83.41 | n.a. | 62.94 | n.a. | 44.02 | n.a. | n.a. | n.a. | n.a. | 51.52 | n.a. | 46.94 |

Interaction Between CA IX and Candidate Compound for Drug

According to the analysis results, two compounds C59 and C34 are particularly promising for actual synthesis for in vitro and in vivo experiments to be performed in the

TABLE 6

| Measure | C45 | C46 | C65 | C66 | C64 | C63 | C56 | C55 | C59 | C51 | C34 | 9FK |
|---|---|---|---|---|---|---|---|---|---|---|---|---|
| Number of atoms within 0.35 um of ligand | 29.19 ± 3.46 | 35.78 ± 4.23 | 29.13 ± 3.06 | 22.28 ± 5.53 | 28.12 ± 3.56 | 24.01 ± 2.89 | 32.70 ± 4.07 | 35.06 ± 4.89 | 45.79 ± 4.23 | 23.49 ± 3.28 | 45.12 ± 4.35 | 18.39 ± 3.26 |
| Number of protein residues within 0.35 nm of ligand | 13.5 ± 1.54 | 14.5 ± 1.53 | 17.18 ± 1.70 | 10.08 ± 1.58 | 12.82 ± 1.76 | 13.56 ± 1.49 | 16.06 ± 1.52 | 16.66 ± 1.66 | 18.14 ± 1.60 | 13.09 ± 1.56 | 16.62 ± 1.49 | 9.41 ± 1.60 |

Interaction Between CA IX and Candidate Compound for Drug

The interaction between 9FKs determined by crystallographic studies was maintained throughout the simulation.

subsequent step, in which the two compounds are (i) 5-chloro-4-methyl-2-sulfamoyl-phenyl) (1E)-4-chloro-5-hydrocy-N-(4-methylanilino)pentaneimidothioate and (ii) (5-chloro-4-methyl-2-sulfamoyl-phenyl) (1E)-N-(4-methyl-2-nitro-anilino)hexamidothioate.

As described above, a target-based drug screening method according to the present invention can contribute to the rapid and efficient discovery of novel target-based drug. That is, the simplicity and rapid computation of inverse quantitative structure-performance relationships analysis and molecular dynamics simulation significantly reduce the cost of drug discovery and enable synthesis and wasteful pharmaceutical tests of false compounds to be avoided.

INDUSTRIAL APPLICABILITY

The present invention can be applied to an initial research stage for drug development because it is possible to significantly reduce investment for discovery of target-based drug and to avoid synthesis and wasteful pharmaceutical tests of false compounds.

What is claimed is:

1. A computer-implemented target-based drug screening method comprising:
   modeling, using a computer processor, a molecular structure of a test compound group against a target molecule, wherein the test compound group comprises one or more compounds that alters an activity of the target molecule, and wherein the target molecule comprises a polypeptide or a nucleic acid, the modeling comprising:
      receiving, by the computer processor, biological experimental data and chemical experimental data of the test compound group, and
      optimizing, by the computer processor, the molecular structure of the test compound group by quantum chemistry modeling of the molecular structure of the test compound on the basis of the biological and chemical experimental data;
   generating, by the computer processor, quantitative structure-performance relationships (QSPR) between one or more structure and performance of the test compound group, the generating comprising:
      producing, by the computer processor, molecular descriptors from the molecular structure of the test compound group by comparing against previously generated drug candidates stored in a database, and
      modeling by the computer processor, the QSPR on the basis of the molecular descriptors;
   acquiring, by the computer processor, an optimum pharmacophore of a novel drug through a numerical inversion of the QSPR; and
   selecting, by the computer processor, one or more drug candidate having a molecular structure similar to the optimum pharmacophore from the test compound group, the selecting comprising:
      verifying, by the computer processor, an optimum candidate based on images generated by the computer processor performing molecular dynamics simulation on data representing a plurality of complexes each comprising one of the selected drug candidates and the target molecule, the drug candidate data having different lipophilicity values associated with properties of the optimum candidate,
      wherein verifying the optimum candidate is based at least in part on the lipophilicity values.

2. The method according to claim 1, wherein, in the QSPR, the performance comprises one or more performances selected from among biological activity, inhibitory activity, the lipophilicity, toxicity, metabolic stability and blood-brain barrier permeability.

3. The method according to claim 1, wherein the generating further comprises:
   selecting one or more molecular descriptors from among the produced molecular descriptors; and
   using, in the modeling of the QSPR, a genetic algorithm using the selected molecular descriptors, wherein the molecular descriptors in the modeling of the QSPR is the selected molecular descriptors.

4. The method according to claim 1, wherein, during the acquiring by the computer processor, the optimum pharmacophore of the novel drug is acquired through a numerical inversion process according to Expression 2, $$x^* = \operatorname{argmax} \sqrt{(\log \hat{k}_w - \log k_{w,ref})^2 + (\log \hat{k}_i - \log k_{i,ref})^2} \quad \text{[Expression 2]}$$

$$\text{s.t } [\log \hat{k}_w, \log \hat{k}_w]^T = C\hat{t}$$

$$\hat{t} = Px$$

$$\hat{t}^T S_{t^{-1}} t \le c_1$$

$$|P\hat{t} - x| \le c_2$$

wherein:
   x is a vector of molecular descriptors of a novel drug candidate,
   x* is a vector of molecular descriptors of an optimal drug calculated from a mathematical programming formula of Expression 2,
   C is an output variable loading matrix of partial least squares (PLS),
   t is a score vector of input variables (being molecular descriptors x herein),
   P is a loading matrix of PLS,
   ^ is a prediction value produced by a PLS model,
   $S_t$ is a sample covariance matrix of t, $c_1$ and $c_2$ are appropriate constants,
   s.t is shorthand for "such that",
   $\hat{T}^T$ is a transposed matrix of the score vector of input variables predicted by the PLS model,
   log $\hat{k}_w$ is a lipophilicity value predicted by the PLS model,
   log $k_{w,ref}$ is a lipophilicity value set by a user, and
   log $k_{i,ref}$ is an activity value set by the user.

5. The method according to claim 1, wherein the selecting further comprises:
   rating each novel drug candidate according to an Euclidean distance between the optimum pharmacophore of the novel drug and the molecular structure of the novel drug candidate group; and
   selecting drug candidates that are rated equal to or higher than a predetermined level from among the drug candidates in the novel drug candidate group.

6. The method according to claim 1, wherein the selecting further comprises selecting the one or more drug candidate data having a maximum lipophilicity value.

* * * * *